United States Patent [19]

Powell

[11] Patent Number: 4,486,219

[45] Date of Patent: Dec. 4, 1984

[54] 6-OXABICYCLO[3.2.1]OCTANE DERIVATIVES AND COMPOSITIONS AND METHODS FOR CONTROLLING PLANT GROWTH

[75] Inventor: James E. Powell, Ripon, Calif.

[73] Assignee: Shell Oil Company, Houston, Tex.

[21] Appl. No.: 487,326

[22] Filed: Apr. 21, 1983

[51] Int. Cl.³ .................... A01N 43/12; C07D 307/00
[52] U.S. Cl. ................................. 71/88; 71/90;
71/92; 71/93; 71/94; 71/95; 544/216; 544/335;
546/139; 546/152; 546/180; 546/269; 548/134;
548/203; 548/206; 548/235; 548/249; 548/262;
548/336; 548/374; 548/525; 549/60; 549/463
[58] Field of Search ............... 549/463, 60; 71/88,
71/90, 92, 93, 94, 95; 544/216, 335; 546/139,
152, 180, 269; 548/134, 203, 206, 235, 249, 262,
336, 525, 374

[56] References Cited

U.S. PATENT DOCUMENTS 3,647,823  3/1972  Isard et al. .................... 549/463

Primary Examiner—Henry R. Jiles
Assistant Examiner—Bernard I. Dentz

[57] ABSTRACT

A compound of the formula

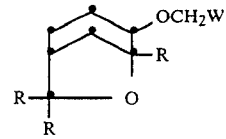

wherein each R is H or alkyl and W is an optionally substituted unsaturated, cycloalkyl, secondary alkyl, aromatic or heterocyclic group, are useful as plant growth regulators and herbicides. The corresponding 6-oxabicyclo[3.2.1]octan-4-ols and 6-oxabicyclo[3.2.1]octan-4-ones are novel intermediates.

11 Claims, No Drawings

6-OXABICYCLO[3.2.1]OCTANE DERIVATIVES AND COMPOSITIONS AND METHODS FOR CONTROLLING PLANT GROWTH

BACKGROUND OF THE INVENTION

Field of the Invention

The present invention relates to novel 6-oxabicyclo[3.2.1]octane derivatives, their use as plant growth regulators and herbicides and to compositions containing these derivatives.

SUMMARY OF THE INVENTION

The present invention is directed to novel 6-oxabicyclo[3.2.1]octane derivatives of formula I

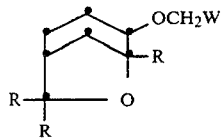

wherein each R is independently a hydrogen atom or an alkyl group containing 1 to 4 carbon atoms; and W is an optionally substituted unsaturated group containing up to 4 carbon atoms, a cycloalkyl group containing 3 to 10 carbon atoms, a secondary alkyl group containing 3 to 10 carbon atoms, an aromatic group containing up to 14 carbon atoms or a heterocyclic group containing up to 14 carbon atoms. The compounds are useful as herbicides and to control the growth of plants.

In the derivatives of formula I, preferably, each R is independently a methyl or an ethyl group. In one embodiment of the invention, each R is preferably a methyl group.

In the derivatives of formula I, preferably W is an ethynyl group, a 2-pyridinyl group or a phenyl group optionally substituted by 1 or 2 chlorine or fluorine atoms or methyl groups. In one embodiment of the invention, W is a 2-chlorophenyl, a 2-fluorophenyl or a 2-methylphenyl group.

Non-limiting species of the derivatives of formula I include
4-(2-fluorobenzyloxy)-5,7,7-triethyl-6-oxabicyclo[3.2.1]octane,
4-(2-pyridinylmethoxy)-5,7,7-trimethyl-6-oxabicyclo[3.2.1]octane,
4-(2-methylbenzyloxy)-7,7-diethyl-5-methyl-6-oxabicyclo[3.2.1]octane,
4-(2-propynyloxy)-5,7,7-trimethyl-6-oxabicyclo[3.2.1]octane,
4-(2-pyrimidinyloxy)-6-oxabicyclo[3.2.1]octane, and
4-(2-triazinyloxy)-5,7,7-triethyl-6-oxabicyclo[n 3.2.1]octane.

Compounds that possess substantially the same plant growth regulator or herbicidal utility as those described herein and which can be prepared in like manner are equivalents thereof and include compounds wherein, for example, W is an unsaturated, aromatic or heterocyclic moiety, or cyclopropyl or 1-methylcyclopropyl, including but not limited to cyano, naphthyl, imidazolyl, triazolyl, thiadiazolyl, 2-quinolinyl, 1-isoquinolinyl, pyrrolyl, cyclohexenyl, N-methylimidazol(-2-)yl, N-methylpyrazol(-2-)yl, isoxazolyl, oxazolyl, isothiazolyl, thiazolyl, thienyl, 5-methyl-2-furanyl, triazinyl, pyrimidinyl, and the like.

The derivatives of formula I of the invention exhibit geometrical and optical isomerism and may be prepared in geometrical and/or optical forms, and as racemates. The various individual optical and geometrical forms and various combinations of the derivatives of the invention usually have some difference in herbicidal or plant growth control properties. The present invention contemplates all these active forms. The derivatives of formula I that have the WCH$_2$O group endo (with respect to the methano bridge) usually have the highest activity. Moreover, the derivatives of the formula I of the invention also are useful as solvents or dispersing agents, e.g. for paints, pigments, polymers and synthetic fibers, and as plastisizers, e.g. for vinyl resins. These latter uses are irrespective of stereoisomerism.

The derivatives of formula I of the invention are prepared by an etherification reaction which introduces the group CH$_2$W. The etherification is conducted by treating the corresponding 6-oxabicyclo[3.2.1]-octan-4-ol derivative with a compound of the formula WCH$_2$X in which W is defined as in formula I above and X is a halogen atom, such as bromine, chlorine or iodine, or is a mesyloxy, tosyloxy group or the like, in the presence of a base and, preferably, an inert diluent. The base is suitably an alkali metal hydride, hydroxide or carbonate, including, for example, sodium hydride, sodium hydroxide, potassium carbonate and the like. Inert diluents (solvents) are suitably organic solvents, such as ethers, aromatic hydrocarbons and the like, including, for example, diethyl ether, tetrahydrofuran, dimethyl sulfoxide, toluene, methylene chloride and the like. The reaction is usually carried out under normal pressures and ambient temperatures. Suitable temperatures of the reaction include those from about 0° C. to about 120° C., preferably from about 20° C. to about 100° C. The reaction can be conducted in a two-phase system, preferably in the presence of a phase-transfer catalyst. For example, such a system is an aqueous sodium or potassium hydroxide solution with toluene or methylene chloride with a catalyst, such as an ammonium compound, including tetra-n-butylammonium chloride, bromide or hydrogen sulfate, triethylbenzylammonium chloride and the like.

The derivatives of formula I are recovered and isolated by conventional techniques.

The corresponding 6-oxabicyclo[3.2.1]octan-4-ols and 6-oxabicyclo[3.2.1]octan-4-ones are also novel derivatives and have the formula II

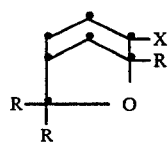

wherein each R is independently a hydrogen atom or an alkyl group containing from 1 to 4 carbon atoms; and X is —OH or =O. In the novel derivatives of formula II, preferably each R is independently a methyl or ethyl group. In one embodiment of the invention, each R is a methyl group.

The derivatives of formula II can be prepared by multistep conventional procedures from acrolein or an alkyl vinyl ketone in which the alkyl portion corresponds to an R in formula II at the 5- and 7-positions. For example, depending on the substitution desired in the derivative of formula II, either acrolein or an alkyl vinyl ketone is dimerized by conventional procedures, such as by heating, to give the dimer, a 2-acyl-3,4-dihydro-2H-pyran derivative.

The dimer is olefinated by a modified Wittig procedure, such as in the presence of methyltriphenylphosphonium bromide and dimsyl sodium in dimethyl sulfoxide, to give a 2-alkenyl-substituted-3,4-dihydro-2H-pyran derivative.

The 2-alkenyl-substituted-3,4-dihydro-2H-pyran derivative is rearranged by conventional procedures, e.g. flow-system pyrolysis, to give the corresponding cyclohexenylmethanone derivative.

The above three steps can be conducted by procedures of the general type described in G. Buchi and J. E. Powell, Jr., *J. Amer. Chem Soc.*, 1970, 92(10), page 3126.

The cyclohexenylmethanone derivative is treated with an appropriate Grignard reagent, e.g. RMgBr, in which R is one of the geminal alkyl substituents desired at the 7-position in formula II, to give, e.g. the alpha,alpha,3-trialkyl-3-cyclohexene-1-methanol derivative.

This alcohol is epoxidized and cyclized, e.g. by treatment with a peroxy acid followed by an acid, such as p-toluenesulfonic acid, to give the desired 6-oxabicyclo[3.2.1]octan-4-ol, usually as a mixture of stereoisomers. This product can be used in etherification directly or can be converted into the corresponding ketone, a 6-oxabicyclo[3.2.1]octan-4-one, e.g. by oxidation with a suitable agent, such as oxalyl chloride-dimethyl sulfoxide, followed by addition of triethylamine. This ketone is converted into predominantly the endo-alcohol by reduction, e.g. with lithium tri(sec-butyl)borohydride in tetrahydrofuran.

ILLUSTRATIVE EMBODIMENTS

The invention is illustrated by the following embodiments which describe the preparation of typical species of the invention. The embodiments are for illustration and should not be regarded as limiting the invention in any way. The identity of the products, including intermediates, was confirmed by elemental, infrared or nuclear magnetic resonance spectral (NMR) analyses as necessary.

EMBODIMENT I alpha,alpha,3-Trimethyl-3-cyclohexene-1-methanol

To 90 ml of dry tetrahydrofuran maintained in an inert atmosphere at −60° C. was added 45.3 ml of a 3.0M solution of methylmagnesium bromide in diethyl ether followed by dropwise addition of 15.6 g of 5-acetyl-1-methylcyclohexene in a solution of 50 ml dry tetrahydrofuran. The reaction mixture was warmed to −20° C. and stirred for two hours. The resulting reaction mixture was poured into 150 ml of chilled, saturated ammonium chloride solution and extracted three times with 300 ml portions of diethyl ether. The combined extracts were washed successively with 300 ml of water and 300 ml of saturated sodium chloride, dried (MgSO$_4$) and concentrated in vacuo to leave 17.1 g of a pale yellow oil. Distillation of the oil gave 10.7 g of the desired product as a colorless oil, b.p. 63°–65° C. (0.65 mm).

EMBODIMENT II 5,7,7-Trimethyl-6-oxabicyclo[3.2.1]octan-4-ol, exo, endo mixture To a magnetically stirred mixture of 300 ml of 1N aqueous sodium bicarbonate and 24.9 g of alpha,alpha,3-trimethyl-3-cyclohexenemethanol dissolved in 600 ml of methylene chloride was added dropwise 33.8 g of 85% m-chloroperbenzoic acid. The resulting reaction mixture was stirred one hour at room temperature, then diluted with 300 ml of methylene chloride. The organic phase was separated and washed successively with 400 ml each of saturated aqueous sodium bisulfite, 1N sodium hydroxide, water and saturated aqueous sodium chloride, dried (Na$_2$SO$_4$) and concentrated in vacuo to leave 21.6 g of a colorless oil predominant in the epimers of the desired intermediate. To 21.3 g of this crude epoxidation reaction mixture in 500 ml of methylene chloride at 0° C. was added 0.52 g of p-toluenesulfonic acid monohydrate. The resultant solution was stirred at room temperature for one and one-half hours. The resulting reaction mixture was washed successively with 150 ml each of 1N sodium hydroxide, water and saturated aqueous sodium chloride, dried (MgSO$_4$) and concentrated in vacuo to leave 20.5 g of a viscous, colorless oil. Distillation of the oil gave 16.3 g of the desired product as a colorless oil, b.p. 68°–73° C. (0.09 mm), predominate (2:1) in the exo- versus endo- alcohol form.

EMBODIMENT III 5,7,7-Trimethyl-6-oxabicyclo[3.2.1]octan-4-one

To a solution of 6.72 g of oxalyl chloride in 150 ml of methylene chloride at −60° C. was added dropwise 8.24 g of dimethyl sulfoxide in 20 ml of methylene chloride. After stirring for 10 minutes at −60° C. under a nitrogen atmosphere, a solution of 7.50 g of 5,7,7-trimethyl-6-oxabicyclo[3.2.1]octan-4-ol in 40 ml of methylene chloride was added dropwise. A white precipitate formed. After stirring in the cold for 15 minutes, 22.22 g of triethylamine was added in a stream via syringe. The reaction mixture was allowed to rise to room temperature and after 15 minutes was poured into 200 ml of ice water. The resulting phases were separated and the aqueous phase was extracted with two 100 ml portions of methylene chloride. The combined organic phases were washed twice with 100 ml portions of saturated aqueous sodium chloride, dried (MgSO$_4$) and concentrated in vacuo to leave 9.07 g of an orange liquid containing some beige solid. This crude mixture was diluted with hexane and filtered. The filtrate was dried (MgSO$_4$) and concentrated in vacuo to leave 8.06 g of orange liquid. Vacuum distillation of the liquid gave two fractions of the desired product; 4.35 g, b.p. 78°–85° C. (4 mm) of 82% purity by GLC and 1.86 g, b.p. 85°–93° C. (4 mm) of 95% purity by GLC.

EMBODIMENT IV 5,7,7-Trimethyl-6-oxabicyclo[3.2.1]octan-4-ol, endo isomer

To a solution of 24 ml of a 1M solution of lithium tri(secbutyl)borohydride in tetrahydrofurane at −70° C. was added dropwise 3.49 g of 5,7,7-trimethyl-6-oxabicyclo[3.2.1]octan-4-one in 3 ml of tetahydrofuran. The resulting solution was stirred under nitrogen for one hour at −70° C. and one hour at room temperature. Then while controlling the temperature at 0° C., the following were successively added: 2.6 ml of water, 5.2 ml of ethanol, 19.2 ml of 10% sodium hydroxide solution and dropwise 8.5 ml of 30% hydrogen peroxide solution. The resulting reaction mixture was stirred for one hour at 25° C., then saturated with solid potassium carbonate and extracted four times with 50 ml portions of a 1:1 solvent mixture of diethyl ether and tetrahydrofuran. The combined organic extracts were washed with 50 ml of saturated aqueous sodium chloride, dried ($Na_2SO_4$) and concentrated in vacuo to leave 6.44 g of an opaque, colorless oil. Kugelrohr distillation of the oil gave 3.13 g of the desired product as a colorless oil, b.p. 71° C. (0.35–0.15 mm), predominate (4:1) in the endo versus exo alcohol form.

EMBODIMENT V endo-4-((2-methylphenyl)methoxy)-5,7,7-trimethyl-6-oxabicyclo[3.2.1]octane A 6.84 g portion of a 60% oil dispersion of sodium hydride was washed with pentane to remove the oil and then suspended in 25 ml of dimethylformamide. Then at 4° C. and under nitrogen a solution of 2.93 g of 5,7,7-trimethyl-6-oxabicyclo[3.2.1]octan-4-ol (4:1 endo:exo) in 15 ml of dimethylformamide was added dropwise. Then at 4° C., a solution of 3.51 g of 2-methylbenzyl bromide in 10 ml of dimethylformamide was added dropwise. After two hours of stirring at room temperature, the reaction mixture was diluted with 150 ml of ice water and extracted five times with 75 ml portions of hexane. The combined organic extracts were washed with 75 ml portions of water and of saturated aqueous sodium chloride, dried ($MgSO_4$), and concentrated in vacuo to leave 8.6 g of an orange oil. Purification of the oil by chromatography on silica gel using the dry column technique and 24:1 hexane-tetrahydrofuran as eluent gave 2.3 g of the desired product as a colorless oil having a 98.5:1.5 ratio of endo:exo isomers by GLC.

EMBODIMENT VI endo-4-((2-Fluorophenyl)methoxy)-5,7,7-trimethyl-6-oxabicyclo[3.2.1]octane Following procedures similar to those described in Embodiment V above, reaction of 2.89 g of 5,7,7-trimethyl-6-oxabicyclo[3.2.1]octan-4-endo-ol with 3.59 g of 2-fluorobenzyl bromide gave 11.1 g of an amber oil. Chromatographic purification as above gave 2.61 g of the desired product as a colorless oil.

EMBODIMENT VII endo-2-(Phenylmethoxy)-1,6,6-trimethyl-7-oxabicyclo[3.2.1]octane Following procedures similar to those described in Embodiment V above, reaction of 0.80 g of 5,7,7-trimethyl-6-oxabicyclo[3.2.1]octan-4-endo-ol with 0.94 g of benzyl bromide gave 1.45 g of a yellow oil. Chromatographic purification as above gave 0.91 g of the desired product as a colorless oil.

The invention includes a method of regulating plant growth, including combating unwanted plants, which comprises applying to the locus an effective amount of a compound of Formula I. For example, the compound can change plant morphology, depress the growth of plants or kill plants. As herbicides, they appear to be more effective when applied preemergence or pre-plant incorporated, particularly to control grassy weeds. For application, the compound generally is applied most effectively by formulating it with a suitable inert carrier or surface active agent, or both. The invention therefore also includes compositions suitable for regulating plant growth, including combating unwanted plants, such compositions comprising an inert carrier or surface-active agent, or both, and as active ingredient at least one compound of formula I.

The term "carrier" as used herein means an inert solid or fluid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, herbicides, or fungicides, are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable fluid carriers are water, alcohols such as, for example, isopropanol, glycols; ketones such as, for example, acetone, methyl ethyl ketone, isophorone, methyl isobutyl ketone and cyclohexanone; ethers such as, for example, diethyl ether and cellosolves; aromatic hydrocarbons such as, for example, benzene, toluene and xylene; petroleum fractions such as, for example, kerosene, light mineral oils; chlorinated hydrocarbons such as, for example, carbon tetrachloride, perchloroethylene, trichloroethane, including liquefied, normally vaporous, gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkyl-aryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25, 50 or 75% by weight of the active compound and usually contain, in addition to the solid carrier, 3-10% by weight of a dispersing agent, 15% of a surface-active agent and, where necessary, 0-10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5-10% by weight of the active compound. Granules are usually prepared to have a size between 10 and 100 BS mesh (1.676-0.152 mm), and may be manufactured by agglomeration or impregnation techniques. Generally, granules will contain 0.5-25% by weight of the active compound, 0-1% by weight of additives such as stabilizers, slow release modifiers and binding agents. Emulsifiable concentrates usually contain, in addition to the solvent and, when necessary, cosolvent, 10-50% weight per volume of the active compound, 2-20% weight per volume emulsifiers and 0-20% weight per volume of appropriate additives such as stabilizers, penetrants and corrosion inhibitors. Suspension concentrates are compounded so as to obtain a stable, non-sedimenting, flowable product and usually contain 10-75% weight of the active compound, 0.5-5% weight of dispersing agents, 1-5% of surface-active agents, 0.1-10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick, mayonnaise-like consistency.

The compositions of the invention may also contain other ingredients, for example, other compounds possessing pesticidal, especially insecticidal, acaricidal, herbicidal or fungicidal properties, as are appropriate to the intended purpose.

Growth regulator or protection of a locus or area from undesirable plants is effected by applying a compound of Formula I, ordinarily in a composition of one of the aforementioned types, to soil in which the seeds of the unwanted plants are present, or to the foliage of the unwanted plants. The active compound, of course, is applied in an amount sufficient to exert the desired action.

The amount of the compound of the invention to be used in regulating plant growth, including combatting undesired plants, will naturally depend on the condition of the plants, the degree of activity desired, the formulation used, the mode of application, the climate, the season of the year, and other variables. Recommendations as to precise amounts are, therefore, not possible. In general, however, application to the locus to be protected of from 0.1 to 10.0 kilograms per hectare of the compound of Formula I will be satisfactory.

EXAMPLES OF ACTIVITY WITH RESPECT TO PLANTS

In the following examples, the species of plants that were tested were:

Barnyardgrass (watergrass)—*Enchinochloa crus-galli*
Large crabgrass—*Digitaria sanguinalis*
Downy brome—*Bromus tectorum*
Yellow foxtail—*Setaria lutescens*
Redroot pigweed—*Amaranthus retroflexus*
Sicklepod—*Cassia obtusifolia*
Velvetleaf *Abutilon theophrasti*
Garden cress—*Lepidium sativum*
Johnsongrass—*Sorghum halepense*
Mustard—*Brassica kaber*
Grain sorghum—*Sorghum vulgare* (Pioneer 265)
Corn—*Zea maize* (deKalb X363)
Cotton—*Gossypium hirsutum* (Acala SJ-2)
Soybean—*Glycine max* (Amsoy 71)
Wheat—*Triticum aestivum* (Cajeme 71)
Sugar beet—*Beta vulgaris*
Cocklebur—*Xanthum pennsylvanicum*

PRIMARY TESTS—PREEMERGENE ACTIVITY

The preemergence (soil) activity of compounds of the invention was evaluated by planting seeds of barnyardgrass, garden cress, downy brome, velvetleaf, yellow foxtail, and sicklepod in test tubes, nominally measuring 25×200 mm, filled about three-quarters full of untreated soil, in each case covered on top with about 2.5 cubic centimeters of soil treated with a certain amount of the test compound. The treated soil applied to the tubes containing the barnyardgrass and cress seeds contained one milligram of the test compound per tube, and contained 0.1 mg of the test compound per each tube containing the seeds of the other plants. The dosages were approximately 22 and 2.2 lb of test compound per acre, respectively. The seeds were planted on top of the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
| --- | --- |
| 9 | No living tissue |
| 8 | Plant severely damaged and expected to die |
| 7 | Plant badly damaged, but expected to live |
| 6 | Moderate damage, but complete recovery expected |
| 5 | Intermediate damage (probably unacceptable for crop plants) |
| 3-4 | Observable damage |
| 1-2 | Plant slightly affected, possibly by the chemical, possibly due to biological variability |
| 0 | No visible effect |

PRIMARY TESTS—POSTEMERGENCE ACTIVITY

The postemergence (foliar) activity of compounds of the invention was evaluated by spraying 10-day-old large crabgrass plants, 13-day-old redroot pigweed plants, 6-day-old Johnsongrass plants, 9-day-old velvetleaf plants, 9-day-old yellow foxtail plants and 9-day-old sickle-pod plants to runoff with a liquid formulation of the test compound. The crabgrass and pigweed plants were sprayed with 2.4 ml of a 0.25% solution (about 10 lb of the test compound per acre), and other plants were sprayed with 2.4 ml of a 0.025% solution (about 1 lb of the test compound per acre). The sprayed plants were held under controlled conditions of temperature, moisture and light for 7 to 8 days, and the effect of the test compound was then evaluated visually, the results being rated on the 0 to 9 scale described above.

Results of the preemergence and postemergence activity tests conducted on the compounds of the invention are set forth in Table 1.

TABLE I

| | HERBICIDAL ACTIVITY | | | | | | | | | | | |
|---|---|---|---|---|---|---|---|---|---|---|---|---|
| | Preemergence (soil) | | | | | | Postemergence (Foliar) | | | | | |
| Embodiment | Barnyard-grass | Garden Cress | Downy Brome | Velvet-leaf | Yellow Foxtail | Sickle-pod | Crab-grass | Pig-weed | Johnson-grass | Velvet-leaf | Yellow Foxtail | Sickle-pod |
| V | 9 | 7 | 7 | 6 | 7 | 5 | 5 | 5 | 3 | 5 | 6 | 2 |
| VI | 9 | 8 | 9 | 7 | 9 | 7 | 8 | 5 | 2 | 4 | 6 | 3 |
| VII | 9 | 8 | 8 | 6 | 7 | 6 | 7 | 3 | 3 | 3 | 6 | 0 |

What is claimed is:

1. A compound of the formula

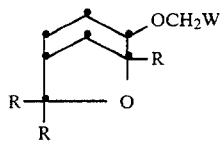

wherein each R is independently a hydrogen atom or an alkyl group containing 1 to 4 carbon atoms; and W is an ethynyl group, a cyano group, a cyclohexenyl group or a phenyl group optionally substituted by 1 or 2 chlorine or fluorine atoms or methyl groups a cycloalkyl group containing 3 to 10 carbon atoms, a secondary alkyl group containing 3 to 10 carbon atoms, or a heterocyclic group selected from an imidazolyl, a triazolyl, thiadiazolyl, 2-quinolinyl, 1-isoquinolinyl, pyrrolyl, N-methylimidazol-2-yl, N-methylpyrazol-2-yl, isoxazolyl, oxazolyl, isothiazolyl, thiazolyl, thienyl, 5-methyl-2-furanyl, triazinyl, pyrimidinyl, or 2-pyridinyl group.

2. A compound according to claim 1 wherein W is an ethynyl group, a 2-pyridinyl group or a phenyl group optionally substituted by 1 or 2 chlorine or fluorine atoms or methyl groups.

3. A compound according to claim 2 wherein each R is independently a methyl or ethyl group.

4. A compound according to claim 3 wherein each R is a methyl group.

5. A compound according to claim 4 wherein W is 2-chlorophenyl.

6. A compound according to claim 4 wherein W is a 2-fluorophenyl group.

7. A compound according to claim 4 wherein W is a 2-methylphenyl group.

8. A compound according to claim 4 wherein W is phenyl.

9. A plant growth regulating composition comprising an effective amount of a compound according to claim 1 and at least one inert carrier or surface-active agent.

10. A method of regulating plant growth at a locus comprises applying to the locus or the plant an effective amount of a compound according to claim 1.

11. A method according to claim 10 wherein the plant growth is regulated by depressing growth of the plant or by killing the plant.

* * * * *